United States Patent [19]

Gerling et al.

[11] Patent Number: 4,487,070

[45] Date of Patent: Dec. 11, 1984

[54] AUTOMATIC PRODUCTION CONTROL OF EXTENDED WORK PIECES

[75] Inventors: Erich Gerling; Karl-Heinz Schlusnus, both of Hamm; Hans-Jürgen Wahl, Münster, all of Fed. Rep. of Germany

[73] Assignee: Hoesch Aktiengesellschaft, Dortmund, Fed. Rep. of Germany

[21] Appl. No.: 410,946

[22] Filed: Aug. 24, 1982

[30] Foreign Application Priority Data

Sep. 1, 1981 [DE] Fed. Rep. of Germany ....... 3134482

[51] Int. Cl.³ .............................................. G01N 29/04
[52] U.S. Cl. ........................................ 73/609; 73/599; 73/620; 73/628
[58] Field of Search ................. 73/598, 609, 615, 616, 73/620, 622, 628

[56] References Cited

U.S. PATENT DOCUMENTS

| | | | |
|---|---|---|---|
| 3,274,822 | 9/1966 | Stanya | 73/628 |
| 3,552,191 | 1/1971 | Heseding | 73/625 |
| 3,791,199 | 2/1974 | Toth et al. | 73/628 |
| 3,888,114 | 6/1975 | Adams, Jr. et al. | 73/628 |
| 4,137,779 | 2/1979 | Wustenberg et al. | 73/628 |
| 4,305,297 | 12/1981 | Ries et al. | 73/628 |
| 4,395,911 | 8/1983 | Macecek | 73/622 |

*Primary Examiner*—Howard A. Birmiel
*Attorney, Agent, or Firm*—Horst M. Kasper

[57] ABSTRACT

An ultrasonic defect monitor for a moving workpiece is disclosed, including first and second test probes on opposite sides of an area of interest. The detected signals are processed for display by both a threshold monitor circuit, and an integrator-threshold-monitor circuit each connected to an output indicating unit for providing defect indications.

14 Claims, 5 Drawing Figures

AUTOMATIC PRODUCTION CONTROL OF EXTENDED WORK PIECES

BACKGROUND OF THE INVENTION

1. Field of the Invention

The present invention relates to an apparatus and a method for the automatic control of production of work pieces where there is to be distinguished between form indicators belonging to deviations from geometrically steady surfaces and material defects.

2. Brief Description of the Background of the Invention Including Prior Art

A generic device is known where form echoes and defect indicators for example at pig mould fin tube and multi-edge profiles are to be distinguished (German Disclosure Laid Out DE-AS No. 22 51 426). In the context of an ultrasonic material test of the circumference of the tube interfering echoes are to be excluded in the defect evaluation, as such echoes can occur at the flanks of the fins at the tube or at the edges of a multi-edge profile. This could result in the disadvantage of the suppression of an error signal as described in column 4, paragraph 4, if the error and the profile edge provide the same time span of the echo signal.

A further method is known from German Disclosure Laid Out DE-AS No. 26 07 783 for the magnetic or magneto-inductive determination of longitudinal defects in long stretched-out metallic test material, where a plurality of sensors are disposed over the work piece region to be tested continuously, where a combined rotary-translatory relative motion is provided between the test sensors and the work piece.

In this defect test the influences of a disturbing zone as represented for example by a long extended welding seam are to be collected and eliminated, in order to detect defects in the material to be tested.

It is disadvantageous in this method that a plurality of sensors are required for the safe determination of longitudinal defects as well as a rotary relative motion is required between the sensors and the work piece. In addition, according to this proposal long extended cracks in the welding seam are disregarded in the evaluation. Furthermore, this method functions only for ferromagnetic materials.

A provision for the determination of surface irregularities at the inner wall of metal tubes is known from German Disclosure Laid Out DE-AS No. 21 42 372, where for example long extended rolling mill defects in seamless rolled tubes are determined by way of a capacitance sensor provision disposed in the interior of the tube.

This provision functions only with an oscillatory or rotary drive for a cross motion to the work piece region to be tested or, respectively, to the longitudinal defects to be determined on the defect containing side of the work piece.

Furthermore, this provision is exclusively applicable for the determination of surface defects; however not for the combined determination of material and surface defects.

SUMMARY OF THE INVENTION

1. Purposes of the Invention

It is an object of the present invention to provide for the assured distinction without gaps of the various longitudinal defect phenomina at the automatic production control of long extended work pieces, where in particular systematical longitudinal defects are to be recognized and distinguished from other material and production defects at connection regions of work pieces such as profile edges, weld reinforcements, excess upset metal, flash trimming defects such as under scraping or residual draw beads.

It is a further object of the invention to provide an optimal test method employing commercial components.

It is another object of the invention to test work piece regions without additional rotating drive for the test apparatus and without employing expensive auxiliary materials with testing speeds of at least 10 to 100 meters per minute in the longitudinal direction of the work piece to be tested.

These and other objects and advantages of the present invention will become evident from the description which follows.

2. Brief Description of the Invention

The present invention provides in one aspect an apparatus for automatic production control of long extended moving work pieces, which comprises a first ultrasonic test probe disposed on a first side of a work piece, a second ultrasonic test probe disposed on a second side of the work piece opposite to the first side, working in pulse echo-method, an emitter for generating ultrasonic pulses at the probes controlled by a test probe change overswitch, a receiver and amplifier for the signals from the first ultrasonic test probe and from the second ultrasonic test probe connected to the respective test probes, a monitor and an integrator-monitor connected to the amplifier, and two output units connected to the monitor, respectively, integrator-monitor.

The output unit can comprise a display, a registering device, a communication interface or an optical or acoustical indicator. The output unit can comprise an analog output.

The integrator-monitor is a comparator for comparing the output of the integrator with a threshold value. Two pairs of ultrasonic probes with different acoustic incidence angles for each pair can be disposed successively on each side of the region of the work piece. A drive can provide relative longitudinal motion between the work piece and the ultrasonic test probes.

There is also provided a method for automatic production control of long extended work pieces which comprises testing the work piece with two ultrasonic test probes, where one probe is disposed at a first location of the work piece and where a second probe is disposed at a second location of the work piece opposite to the first location relative to the region to be inspected, and the probes operating according to the pulse-echo method, moving the work piece relative to the ultrasonic test probes only along a region of the work piece to be tested, providing that at least one pair of ultrasonic test probes provides continuous testing, coordinating the signals received by the ultrasonic test probes along the region of the work piece to the proper side of the work piece, and integrating the side-coordinated signals coming from the ultrasonic test probes.

The side-coordinated signals can be compared with a first predetermined threshold value in a monitor. A separate indication can be provided for possible surpassing of the threshold value. The integrated side-coordinated signals can be compared with a second predetermined threshold value in the integrator-monitor, where the second predetermined threshold value is lower than the first threshold value for the received signals.

A separate indication can be provided for possible surpassing of the second threshold value. The amplitudes of the results of the integrating can be displayed and/or registered. The difference of the integrating results for the side-coordinated signals can be determined. The difference of the integration results can be compared with a third predetermined threshold value. The measured values can be applied to determine form deviations of a work piece from a geometrically continuous surface without simultaneous testing of short material or production defects.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

BRIEF DESCRIPTION OF THE DRAWING

In the accompanying drawing in which are illustrated several of the various possible embodiments of the present invention.

DESCRIPTION OF INVENTION AND PREFERRED EMBODIMENTS

Figure 1:
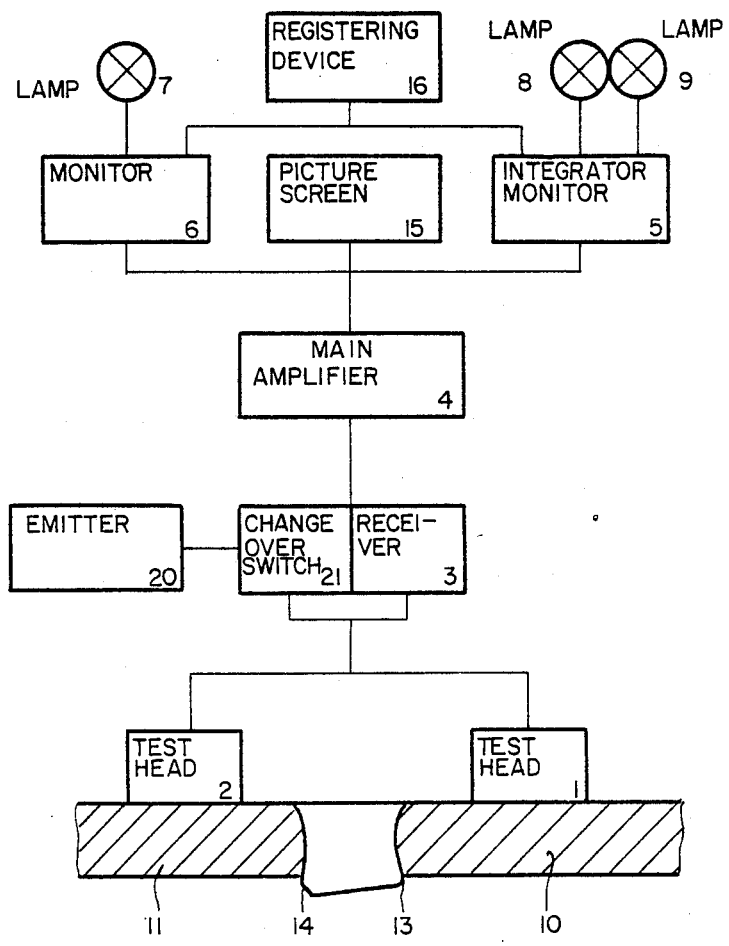
FIG. 1 is a view of a schematic block circuit diagram of the apparatus of the present invention.

In accordance with the present invention there is provided a method for the automatic production control of long extended work pieces with a distinction between form indications based on such positions of a work piece, which deviate from geometrically steady surfaces and from defect indications at the testing of the material, where at least two ultrasonic test probes operating according to the pulse-echo method and serving to determine defects are moved relative to the work piece to be tested. The work piece is moved only along a region of the work piece to be tested relative to the ultrasonic test probes. At least one ultrasonic test probe on each side of the region of the work piece to be tested continuously tests the work piece. The signals received from the ultrasonic test probes along the region of the work piece are collected properly coordinated to the respective side and are on the one hand compared with a first predetermined threshold. On the other hand the received signals are first integrated and then compared with a second predetermined threshold value and possibly the surpassing of the threshold values is separately indicated.

In place of or in addition to the threshold evaluation of the integrating results the amplitudes of the integrating results can be displayed and/or registered. A difference of the integration results can be indicated and/or compared with a third predetermined threshold value. The second predetermined threshold for the results of the integrating can be lower than the first predetermined threshold for a direct evaluation of the received signals.

The method of the present invention can be applied to determine form deviations of a work piece from a geometrical steady surface without simultaneous testing for short material or production defects.

There is also provided an apparatus which comprises ultrasonic test probes, amplifiers, monitor and provisions for displaying, registering and indicating where a monitor is provided as an integrator-monitor (e.g. commercially available type: MC 1711 CG from Messrs Motorola Semiconductors, Phoenix, Ariz. USA) and is further provided with a threshold comparator and/or an analog output for the results of the integration.

Preferably, on each side of the work piece to be tested are disposed successively two ultrasonic test probes with different acoustic incidence angles. The indicating devices can be optical devices and/or acoustic devices.

The invention is based on the observation that for example welding defects are relatively short as compared with welding seam beads or geometric irregularities of the work piece surface generated by a defective trimming. It was further observed that in special application cases, that is during the surveillance of a provision for the removal of inner flashes in welded tubes and in particular for defective deep scraping, inclined scraping or residual beads no conventional ultrasonic wall thickness measuring apparatus can be employed, since the region of the welding seam is much too hot even with worked off outer seam reinforcement in order to be able to work without expensive coupling media. In this case also the positioning of sensing devices in the interior of the tube would pose a problem and would be practically impossible in case of a narrow tube diameter based on the interference caused by the flash trimming chips generated.

According to the invention method it is possible to separate flash trimming defects on the bottom side of the work piece by way of a defect length determination from other welding and material defects upon employment of conventional ultrasonic test probes for the welding defect surveillance directly behind the welding aggregate, which ultrasonic test probes are disposed above the work piece next to the region of the work piece to be monitored. The recognition of welding and material defects is made possible with a first present threshold value. The integration of the signals along the tested region of the work piece and the comparison of the integration results with a second present threshold value thus allows the distinction of long extended defects from other defects despite possibly the same or smaller amplitude height of the different signals.

Based on the possibility of arranging the test probes on the side of a hot welding seam one can operate with commercial ultrasonic test probes in the presence of a usual water coupling. The relative motion between the ultrasonic test probes and the work piece is generated by the work piece running through. An additional drive for the test provision is not required.

A comparison of the integration results of the test traces on both sides of the region of the work piece to be tested provides according to the invention as a difference an information about a possible asymmetry of a long extended geometrical deviation, for example of an inclined deep scraping upon planing of a welding seam reinforcement. According to the invention this difference, that is the asymmetry of the contour, can be very simply and separately displayed or indicated for the two test traces, such that an operator can align the planing tool.

The selection of the ultrasound incidence angle in ultrasonic testing for inner defects is provided as is known depending on the object to be tested or, respectively its shape and possible geometry deviations. Using the invention for testing tubes one should select ultrasonic incidence angles of about 45° and 65° detection of all possible scraping states. If only one ultrasonic incidence angle is used the ultrasonic beam with this angle may be diffusedly reflected at certain geometrical edges resulting from the scraping.

Practical experience has shown that in certain products short material defects are allowable, however long extended, notch like geometrical deviations are not permissible. By way of various threshold values the two signal amplitudes can be evaluated according to the defects present.

Also upon selection of ultrasonic test probes with various ultrasound incidence angles there result different amplitudes at the signal defects.

Referring now to FIG. 1 there are shown the sheet metal pieces 10 and 11, which are connected in the connection region 12 by way of butt welding to a single work piece. The upper weld seam reinforcement in the connection region 12 is worked down completely; the lower welding seam reinforcement shows a defective angle scraping with an inclination from edge 14 to edge 13.

The butt welding of the sheet metal pieces 10, 11 and the removal of the welding seam reinforcements is performed continuously by running through a production plant not shown here with a speed of 50 meters per minute. The direction of motion of the work piece is vertical to the plane of paper.

Two ultrasonic angle test probes 1, 2 with ultrasound incidence angles of 60 degrees of an ultrasound testing provision are disposed stationary on the side of the connection region 12 of the work piece directly opposite behind the provision for removal of the welding seam reinforcements. They operate according to the pulse-echo method and are excited by the emitter 20 and switched via the test probe change over switch 21.

The signals received and preamplified by the receiver 3 of defect echoes and form echoes are fed to the monitor 6 and to the integrator-monitor 5 via a main amplifier 4. A lamp 7 announces the possible surpassing of a preset threshold value of 5 percent or 10 percent of the thickness of the sheet metal by defects, for example a slag inclusion or edge zone defect. Threshold surpassings generated by form defects such as for example defective scraping in the connection region 12 of the sheet metal pieces 10, 11 are reported by the lamps 8, 9, where the lamp 8 is coordinated to the left section and the lamp 9 is coordinated to the right section of the connection region 12. If an inclined scraping is present as here with an inclination from the edge 14 to the edge 13, then only the lamp 8 is switched on and upon horizontal defective scraping both lamps are switched on. The test sensitivity of the ultrasonic angle test probes can be adjusted with the picture screen 15 and their function can be watched.

Figure 2:
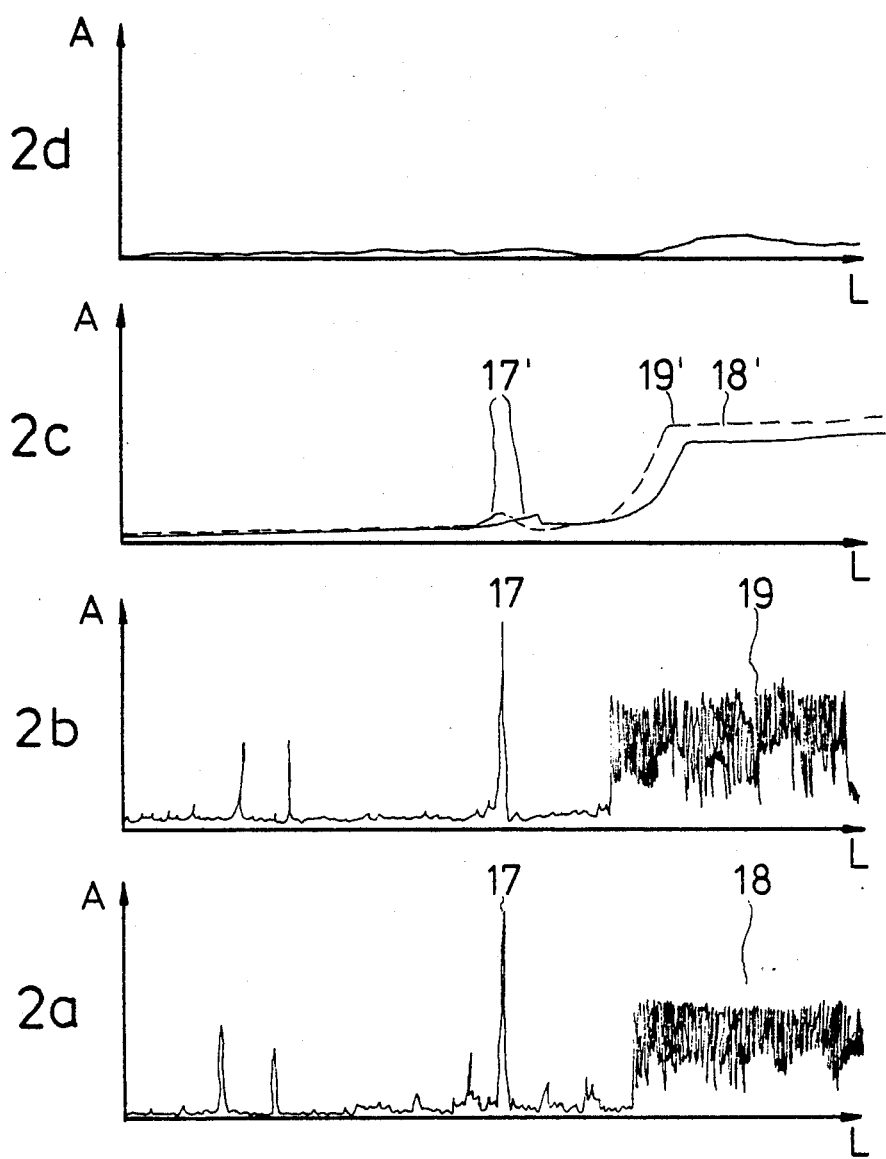
FIG. 2a is a view of a trace of the echo based on defective scraping at the position of the edge 13 of FIG. 1.
FIG. 2b is a view of a trace of the echo based on defects at the position of the edge 14 of FIG. 1.
FIG. 2c is a view of the signal course at the output of the integrator in the integrator-monitor.
FIG. 2d is a view of the difference of the integrator signals 18', 19' of FIG. 2c.

A schematic trace of indicating signals based on defects present in a work piece in a registering device 16 are shown in FIG. 2. The amplitude of the signals is drawn over a longitudinal section of a tested work piece.

FIG. 2a shows the echoes at the ultrasonic angle test probe 1 based on material defects 17 and form defects 18 based on defective scraping at the position of the edge 13 (FIG. 1).

FIG. 2b shows in analogy thereto the echoes of material defects 17 and form defects 19 at the position of the edge 14 (FIG. 1).

FIG. 2c represents the trace of the signal at the output of the integrator monitor 5. The relatively short material defects produce upon integration of the areas under the signal trace according to FIG. 2a only a slight increasing slope 17' of the integrator signal. A longer defect area based on form defects (edges 13, 14) in contrast results in a strongly increasing slope 18', 19' of the integrator signals.

The asymmetry of the form defect and the resulting signal traces 18, 18', 19, 19' are shown in FIG. 2d as difference of the integrator signals 18', 19'.

By way of the above in detail illustrated embodiment of the invention in addition to the inclined scraping of a welding seam reinforcement of course also other geometrical defect forms can be proven in a region of the work piece to be tested such as for example the states: top and/or bottom unscraped, residual beads, plate edge displacement, deep scraping, tool breakage, grooves and drag lines in the work piece.

The invention apparatus and method can also be employed for other applications for example to test the welding seam of longitudinal weld seam tubes and spiral weld tubes, of groove planing, groove milling cutting and the like.

A precondition for the application of the method is only that the contour of the work piece to be tested is continuous in a mathematical sense, that is round, straight and so on.

It will be understood that each of the elements described above, or two or more together, may also find a useful application in other types of system configurations and production control procedures differing from the types described above.

While the invention has been illustrated and described as embodied in the context of an ultrasonic testing device, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. Apparatus for ultrasonic inspection of regions of long extended work pieces comprising
   a first ultrasonic test probe disposed at a first location of a work piece;
   a second ultrasonic test probe disposed at a second location of the work piece opposite to the first location relative to the region to be inspected;
   an emitter for generating ultrasonic pulses; a test probe change over switch connected to each probe;

a receiver for receiving the signals from the first ultrasonic test probe and from the second ultrasonic test probe connected to the respective test probes;

an amplifier for amplifying the signals from the first ultrasonic test probe and from the second ultrasonic test probe connected to the respective test probes;

a threshold monitor connected to the amplifier;

an integrator-threshold-monitor connected to the amplifier;

output indicating units connected to the threshold monitor and integrator-threshold-monitor, respectively, for providing indications of defects in the regions to be inspected; and a drive for providing a relative motion between the work piece and the ultrasonic test probes.

2. The apparatus for automatic production control according to claim 1 where the output unit comprises a display.

3. The apparatus for automatic production control according to claim 1 where the output unit comprises a registering device.

4. The apparatus for automatic production control according to claim 1 wherein the output unit comprises a communications interface.

5. The apparatus for automatic production control according to claim 1 where the output unit comprises an analog output.

6. The apparatus for automatic production control according to claim 1 comprising two opposite pairs of ultrasonic test probes with different acoustic incidence angles for each pair disposed successively on the sides of the region of the work piece.

7. The apparatus for automatic production control according to claim 1 further comprising optical indicator devices connected to the output unit.

8. The apparatus for automatic production control according to claim 1 further comprising acoustic indicator devices connected to the output unit.

9. A method for ultrasonic inspection of regions of long extended work pieces comprising testing the work piece with two ultrasonic test probes disposed in opposite side locations relative to of the region of the work piece which should be tested, and operating according to the pulse-echo method;

moving the work piece relative to the ultrasonic test probes along a direction substantially parallel to the length of the region of the work piece to be tested;

disposing at least one ultrasonic test probe on each desired area of a region of the work piece to be tested and furnishing continuous testing by alternating operation of said test probes;

coordinating the signals received by the ultrasonic test probes along the region of the work piece to the proper side of the work piece relative to the test probe of origin; integrating the side-coordinated signals coming from the ultrasonic test probes;

comparing the side-coordinated signals with a first predetermined threshold value; and providing a separate indication for the possible surpassing of the first threshold value by a received signal from at least one of the probes;

comparing the integrated side-coordinated signals with a second predetermined threshold value, and providing separate indications for the possible surpassing of the second threshold value by either integrated signal for its respective probe.

10. The method for production control according to claim 9 further compromising displaying the amplitudes of the results of the integrating.

11. The method for production control according to claim 9 further comprising registering the amplitudes of the results of the integrating.

12. The method for production control according to claim 9 further comprising determining the difference of the integrating results for the side-coordinated signals.

13. The method for production control according to claim 12 further comprising comparing the difference of the integration results with a third predetermined threshold value.

14. The method for production control according to claim 9 further comprising applying the measured values to determine form deviations of a work piece from a geometrically continuous surface without simultaneous testing of short material or production defects.

* * * * *